(12) United States Patent
Gallagher (10) Patent No.: US 7,023,007 B2
(45) Date of Patent: Apr. 4, 2006

(54) METHODS AND SYSTEMS FOR ALIGNMENT OF DETECTION OPTICS

(75) Inventor: Steven J. Gallagher, Palo Alto, CA (US)

(73) Assignee: Caliper Life Sciences, Inc., Mountain View, CA (US)

(*) Notice: Subject to any disclaimer, the term of this patent is extended or adjusted under 35 U.S.C. 154(b) by 353 days.

(21) Appl. No.: 10/345,699

(22) Filed: Jan. 16, 2003

(65) Prior Publication Data

US 2003/0127610 A1 Jul. 10, 2003

Related U.S. Application Data

(63) Continuation-in-part of application No. 10/197,231, filed on Jul. 16, 2002, now abandoned.

(60) Provisional application No. 60/306,094, filed on Jul. 17, 2001.

(51) Int. Cl.
*G01N 21/86* (2006.01)

(52) U.S. Cl. .............................. 250/559.29; 250/559.4

(58) Field of Classification Search .................... None
See application file for complete search history.

(56) References Cited

U.S. PATENT DOCUMENTS

| | | | |
|---|---|---|---|
| 5,959,291 A | 9/1999 | Jensen | |
| 6,225,635 B1 | 5/2001 | Brewer et al. | |
| 6,246,046 B1 | 6/2001 | Landers et al. | |
| 6,353,475 B1 | 3/2002 | Jensen et al. | |
| 6,399,952 B1 | 6/2002 | Maher et al. | |
| 6,468,763 B1 | 10/2002 | Farinas | |
| 6,900,889 B1 * | 5/2005 | Bjornson et al. | 356/246 |
| 2002/0015147 A1 | 2/2002 | Maher et al. | |
| 2002/0143437 A1 | 10/2002 | Handique et al. | |
| 2002/0179849 A1 | 12/2002 | Maher et al. | |

* cited by examiner

*Primary Examiner*—Que T. Le (57) ABSTRACT

The present invention provides methods and systems for aligning detection optics with a device by obtaining an optical profile of the system and comparing it with a preprogrammed layout of the various optical features of the device. The invention also provides methods of identifying devices by comparing the optical profile with a library of preprogrammed optical profiles of multiple devices.

17 Claims, 8 Drawing Sheets

METHODS AND SYSTEMS FOR ALIGNMENT OF DETECTION OPTICS

CROSS-REFERENCE TO RELATED APPLICATION

This application is a continuation-in-part of U.S. patent application Ser. No. 10/197,231, filed Jul. 16, 2002, now abandoned, which claims the benefit of U.S. Provisional Patent Application Ser. No. 60/306,094, filed Jul. 17, 2001, both of which are incorporated herein by reference in their entirety for all purposes.

BACKGROUND OF THE INVENTION

There has been a growing interest in the manufacture and use of microfluidic devices for the acquisition of chemical and biochemical information. Microfluidic devices typically contain fluid reservoirs connected to a network of microscale channels and chambers through which fluid can flow. Microfluidic devices enable reactions and the detection of reaction products to take place within a single device. Because microfluidic devices operate on small scales, they provide substantial advantages over standard laboratory techniques in terms of analytical throughput, reduced reagent consumption, data precision, process automation, and miniaturization. For example, carrying out complex biochemical reactions in microfluidic devices instead of standard laboratory equipment can reduce reagent usage while increasing reaction speed and throughput. Microfluidic devices are generally part of a fully integrated analysis system that also includes several other components. A fully integrated analysis system that employs one or more microfluidic devices, which can be referred to as a microfluidic system, usually includes at least a material transfer system, a power source, and a detection system. An example of a microfluidic system is any embodiment of the high throughput screening systems described in U.S. Pat. No. 6,046,056, which can be used to screen large numbers of compounds to find compounds having therapeutic properties.

Because of the small dimensions of microfluidic devices, it is often difficult to properly align the microfluidic device within a microfluidic system. Improper alignment can degrade the performance of the system. For example, improper alignment of a detection system over a microfluidic device may impair the ability of a microfluidic system to detect reaction products. Therefore, it becomes necessary to have systems that are capable of properly positioning components such as a detection system with respect to a targeted region of the microfluidic device such as a detection region. The present invention serves this and other needs by providing methods and systems for alignment of detection optics in use with a microfluidic device.

The small dimensions of microfluidic devices may also make it difficult to identify particular microfluidic devices. The inability to identify microfluidic devices may be problematic if an instrument that employs microfluidic devices is capable of using different microfluidic devices. Therefore, it is desirable to have systems that are capable of identifying a microfluidic device. The present invention serves this and other needs by providing methods and systems for identifying a microfluidic device.

SUMMARY OF THE INVENTION

The present invention provides improved microfluidic systems and methods of using these systems for performing laboratory analyses in a convenient and rapid format. In particular, the present invention provides methods and systems for aligning detection optics with respect to microfluidic devices. In one aspect, the present invention provides methods in which an optical profile of a microfluidic device is used to align the detection optics with a targeted region of the microfluidic device. The present invention also provides microfluidic devices with enhanced optical features whereby a distinct optical profile may be obtained for a particular device. In another aspect, the invention provides methods for identification of microfluidic devices by virtue of the distinct optical profile associated with each device. Although described in terms of microfluidic devices, those of skill in the art will appreciate the use of this invention with other devices associated with laboratory analysis systems, such as multiwell plates, and the like.

DETAILED DESCRIPTION

The present invention is generally related to improved microfluidic systems and methods for their use in performing chemical and biochemical analyses of a sample. Specifically, the present invention provides methods and systems for aligning the optical components of a detector over a region of a microfluidic device so as to improve the overall efficiency of a microfluidic system by improving the coordination of its various components. In preferred aspects the methods and systems of the instant invention are used in the detection of light-based signals emanating from microfluidic devices that are part of a microfluidic system capable of detecting such light-based signals. Examples of microfluidic devices compatible with the invention are fused silica capillary devices, capillary electrophoresis (CE) devices, and any other microfluidic devices that contain microscale channels. Particular examples of compatible devices are described in U.S. Pat. No. 5,976,336.

I. Microfluidic Systems

As used herein, the terms "microscale" or "microfabricated" generally refers to structural elements or features of a device that has at least one fabricated dimension in the range of from about 0.1 µm to about 500 µm. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to an element that has one or more fluid passages, chambers or conduits with at least one internal cross-sectional dimension (e.g. depth, width, length, diameter) that is less than 500 µm, and typically between about 0.1 µm and about 500 µm. In the devices of the present invention, the microscale channels or chambers preferably have at least one cross-sectional dimension between about 0.1 µm and 200 µm, more preferably between about 0.1 µm and 100 µm, and often between about 0.1 µm and 20 µm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two or more channels are in fluid communication. The body structure of the microfluidic devices may be an integrated structure or an aggregation of multiple separate parts that fit together to form an aggregate body structure.

Typically, the body structure of the microfluidic devices described herein comprises an aggregation of two or more separate layers that, when appropriately mated or joined together, form a microfluidic device containing channels and/or chambers. Typically, the microfluidic devices described herein will comprise a top portion, a bottom portion, and an interior portion, wherein the interior portion substantially defines the channels and chambers of the device.

Figure 1:
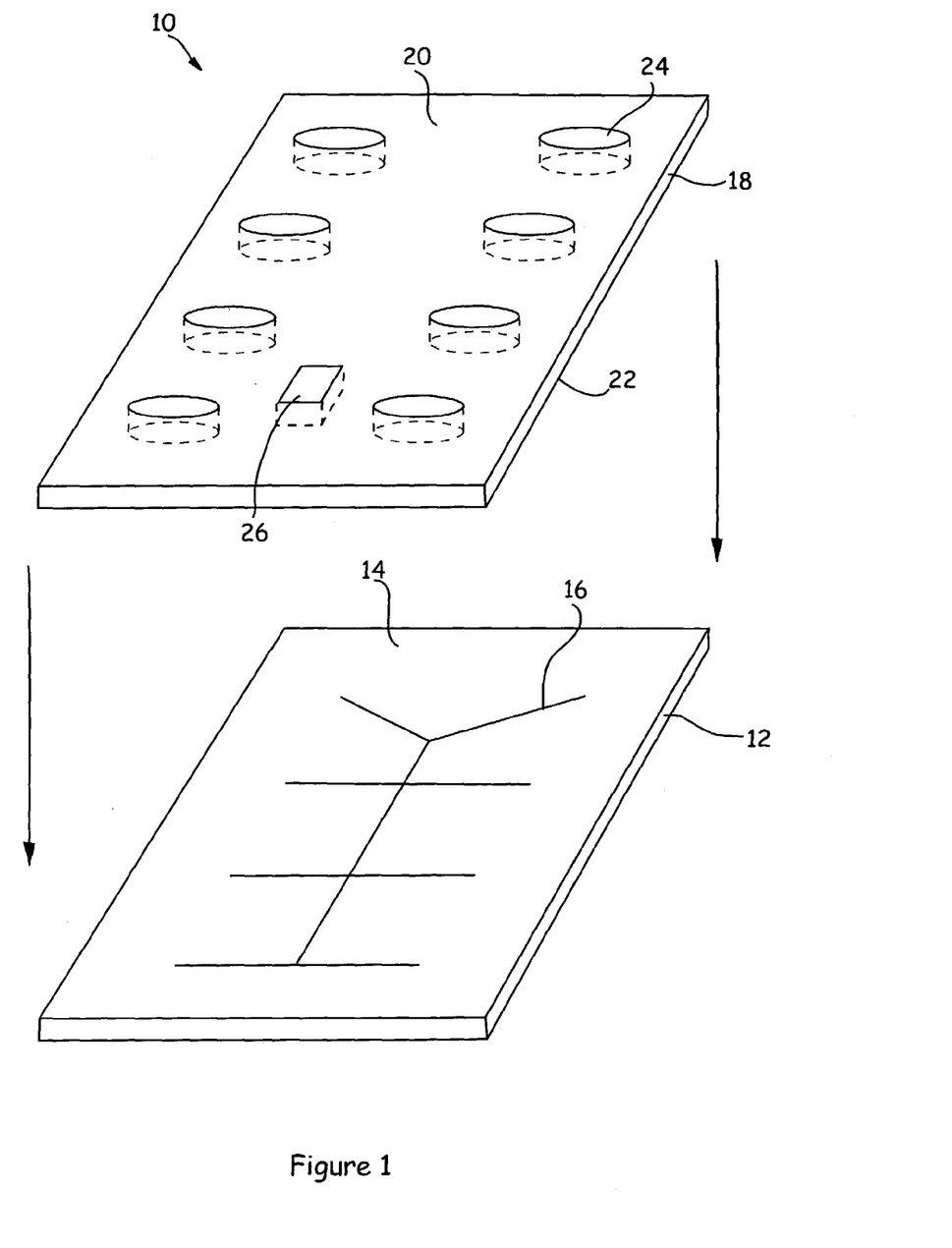
FIG. 1 is a typical microfluidic device.

FIG. 1 illustrates microfluidic device 10 with a two-layer body structure. The bottom portion of the device 12 comprises a solid substrate that is substantially planar in structure, and that has a substantially flat upper surface 14. The top portion of the device 18 comprises a second substantially planar substrate that has a first planar surface 20, and a second surface 22 opposite the first planar surface 20.

A variety of substrate materials may be used for the top and bottom portions of the microfluidic device. Typically, because the devices are microfabricated, substrate materials will be selected based upon their compatibility with known microfabrication techniques such as photolithography, wet chemical etching, laser ablation, air abrasion techniques, injection molding, embossing. The substrate materials are also generally selected for their compatibility with the full range of conditions to which the microfluidic devices may be exposed, including extremes of pH, temperature, salt concentration, and the application of electric fields. Accordingly, in some embodiments, the substrate material may include materials normally associated with the semiconductor industry in which such microfabrication techniques are regularly employed, including silica based materials such as glass or quartz, silicon, polysilicon, and gallium arsenide. In the case of semiconductive materials, it will often be desirable to provide an insulating coating or layer, such as silicon oxide, over the substrate material, and particularly in those applications where electric fields are to be applied to the device or its contents. Although substrates may be planar in structure, it will be appreciated that a variety of other substrate conformations may be utilized, including concave, convex, and tubular structures.

The substrate materials may also comprise polymeric materials such as the plastics polymethylmethacrylate (PMMA), polycarbonate, polytetrafluoroethylene (TEFLON™), polyvinylchloride (PVC), polydimethylsiloxane (PDMS), and polysulfone. Such polymeric substrates are readily manufactured using available microfabrication techniques, as described above, or molded from microfabricated masters, using well known molding techniques, such as injection molding, embossing or stamping, or by polymerizing the polymeric precursor material within the mold (See U.S. Pat. No. 5,512,131). The polymeric substrates may include treated surfaces, including derivatized or coated surfaces, to enhance their utility as a microfluidic device by, for example, providing enhanced fluid direction as described in U.S. Pat. No. 5,885,470. Further, polymeric substrates in accordance with the invention may be fabricated in any of a variety of conformations including planar, tubular, concave, or convex.

In the embodiment shown in FIG. 1, microscale grooves or indentations 16 are fabricated into the upper surface 14 of the bottom substrate 12 as using any of the above described microfabrication techniques. The top portion 18 includes a plurality of apertures, holes or ports 24 that extend from the first planar surface 20 to the second surface 22. When the first planar surface 20 of the top portion of the substrate 18 is mated, in other words placed into contact with, and then bonded to the planar surface 14 of the bottom substrate 12, it covers and seals the grooves and/or indentations 16 in the surface of the bottom substrate 12, to form the channels and/or chambers (i.e., the interior portion) of the microfluidic device. The holes 24 in the top portion of the device are oriented such that they are in communication with at least one of the channels and/or chambers formed in the interior portion of the device from the grooves or indentations 16 in the bottom substrate 12. In the completed device, these holes 24 function as reservoirs for facilitating fluid or material introduction into the channels or chambers of the interior portion of the device, as well as providing ports for coupling controllers for directing movement of materials through and among the channels of the device e.g., pressures sources, electrical sources etc.

In many embodiments, the microfluidic devices will include an optical detection window 26 disposed across one or more channels and/or chambers of the device. Optical detection windows are typically transparent such that they are capable of transmitting an optical signal from the channel/chamber over which they are disposed. If the cover is transparent to the desired wavelengths of light, the optical detection windows could merely be regions of the transparent cover. For visible wavelengths of light, for example, the cover would be transparent if were made of glass or a transparent polymer material. Alternatively, when the substrates used for the top portion 18 of a device are used for the top portion 18 of a device are opaque to the relevant wavelengths of light, one or more transparent detection windows 26 may be placed into an aperture in the top portion 18 of the device.

Microfluidic devices may be used in a variety of applications, including the performance of high throughput screening assays in drug discovery, immunoassays, diagnostics, genetic analysis, and the like. As such, the devices described herein will often include multiple sample introduction ports or reservoirs for the parallel or serial introduction and analysis of multiple samples. Alternatively, these devices may be coupled to a sample introduction port, such as a pipettor, that serially introduces multiple samples into the device for analysis. Examples of such sample introduction systems are described in U.S. Pat. Nos. 5,880,071 and 6,046,056.

II. Detection System

In general, detection of chemical or biochemical reactions involves light based detection of end products using light absorbance, fluorescence, phosphorescence or the like. The light absorbed or emitted from the end product could be of any wavelength including ultraviolet, visible, and infrared. Generally, in the case of microfluidic systems, the detection systems are placed either within or proximal to one or more microchannels, microchambers, micro-reservoirs or conduits of the device, so that the detector is within sensory communication of the device. When a detector is "proximal" to a particular element or region, the detector is in a position such that the detector is capable of detecting a property of the microfluidic device, a portion of the microfluidic device, or the contents of portion of the microfluidic device. The portion of the microfluidic device could be a single channel or chamber, a portion of a single channel or chamber, two or more channels or chambers, or portions of two or more channels or chambers. Typically, in the operation of conventional microfluidic systems, the detection system is oriented substantially perpendicular to the planar body structure of the device. The materials being analyzed in these systems, typically by being subjected to optical analysis for light based signals, are analyzed by being transported along a microscale channel past a detection point where a detectable signal indicative of the presence or absence of some material or condition is measured. In the case of light based detection systems, the signals within these channels typically result from the presence of light emitting substances therein, such as fluorescent or chemiluminescent materials, that indicate the presence or absence of some material or condition.

Many different molecular/reaction characteristics can be detected in the devices of the current invention. As such, any number of detection methods may be employed for the different applications. In the case of optical detection systems, an optical property of a material within a portion of the microchannel network within a microfluidic device is measured. The present invention provides methods for positioning the detection system at a desired location that is proximal to a portion of the microchannel network within a microfluidic device so that the detection system is in sensory communication with the portion via an optical detection window disposed across the portion of the device.

Optical detection systems in accordance with the invention include systems capable of measuring the light emitted from a material, the transmissivity or absorbance of a material, or a material's spectral characteristics such as fluorescence or chemiluminescence. Detectors may optionally detect a labeled compound containing fluorogenic, colorimetric, or radioactive components. The various types of detectors include spectrophotometers, photodiodes, avalanche photodiodes, microscopes, scintillation counters, cameras, diode-arrays, imaging systems, photomultiplier tubes, CCD arrays, scanning detectors, galvo-scanners, film and the like, as well as combinations thereof. Proteins, antibodies, or other components that emit a detectable signal can be flowed past the detector, or alternatively, the detector can move relative to an array to determine molecule position, or, the detector can simultaneously monitor a number of spatial positions corresponding to channel regions such as in a CCD array. Examples of suitable detectors are widely available from a variety of commercial sources known to persons of skill in the art. The Photonics Directory, books 1, 2, 3 and 4, published annually by Laurin Publishing Co., Berkshire Common, P.O. Box 1146, Pittsfield, AM provides common sources for optical components.

Detection systems compatible with the systems and methods of the present invention can optionally comprise a number of different apparatuses. For example, fluorescence can be detected by a photomultiplier tube (PMT), a charge coupled device (CCD), or a photodiode. A photomultiplier tube is an optional aspect of the present invention. A photomultiplier tube converts light (photons) into an electronic signal. In embodiments of the present invention, the location of certain features of a microfluidic device can be determined by detecting a light signal by converting the light signal into an electric signal using a photomultiplier tube. Typically, the magnitude of light signal available for detection is extremely small due to the small dimensions of the microscale channels. For example, the power levels of electrical signals generated by converting the light from detection regions of microfluidic devices in accordance with the present invention are about 0.1 pW to about 10 pW. A PMT therefore is a preferred detection means since it amplifies the signal from each photon of detected light into a larger and more easily measurable pulse of electrons. PMTs are commonly used in many laboratory applications and settings and are well known to those of skill in the art.

Another optional embodiment of the detection systems of the present invention comprises a CCD. CCD cameras can detect even very small amounts of electromagnetic energy, such as that emitted by fluorophores in a microfluidic channel. CCD cameras are made from semi-conducting silicon wafers that release free electrons when light photons strike the wafers. The output of electrons is linearly directly proportional to the amount of photons that strike the wafer. This allows the correlation between the image brightness and the actual brightness of the event observed. CCD cameras are very well suited for imaging fluorescence emission since they can detect even extremely faint events, can work over a broad range of spectrum, and can detect both very bright and very weak events. CCD cameras are well known to those in the art and several suitable examples include those made by Stratagene (La Jolla, Calif.), Alpha-Innotech (San Leandro, Calif.), and Apogee Instruments (Tucson, Ariz.), among others.

Yet another optional embodiment of the detection systems of the invention comprises use of a photodiode to detect fluorescence from molecules in the microfluidic device. Photodiodes absorb incident photons that cause electrons in the photodiode to diffuse across a region in the diode, thus causing a measurable potential difference across the device. This potential can be measured and is directly related to the intensity of the incident light.

Generally, the detection system measures the amount of light emitted from a material, such as a fluorescent or chemiluminescent material. As such, the detection system of the present invention typically includes collection optics that gathers a light based signal transmitted through the detection window or zone and transmits the signal to an appropriate light detector (described in greater detail below). Microscope objectives of varying power, field diameter, and focal length are readily utilized as at least a portion of the collection optics.

The detection system is typically coupled to a computer via an analog to digital or digital to analog converter so that the detected light data may be transmitted to the computer for analysis, storage and data manipulation. One of the more common detection schemes that can be employed in systems in accordance with the present invention is to measure the light emitted from a fluorescent material such a fluorescent indicator dye. In the typical operation of the microfluidic systems that use fluorescence detection, a signal bearing sample material is transported along the microscale channel and past a detection point. In general the detection system includes at least one light source emitting light at one or more excitation wavelengths and a light detector for detecting one or more fluorescent wavelengths. In one embodiment, the sample is irradiated by two different sources, a laser emitting red light and an LED emitting blue light. Both sources operate in a continuous, rather than pulsed, mode.

The sample fluoresces at multiple wavelengths when irradiated with light of the appropriate wavelength. A detector detects the fluorescence emitted by the sample. Both the excitation light and the emitted fluorescence pass through a common lens assembly thereby creating a common beam path for both the excitation and the emission light. Filters are used both in conjunction with the source and with the detectors in order to minimize the background radiation falling on the detectors, thereby increasing the signal to noise ratio. To be able to detect the fluorescence the light detector is located proximal to a detection window overlying the portion of the microchannel network that emits the fluorescence.

Typically, a detection system in accordance with this invention comprises a number of optical components including lenses, lasers, LEDs, filters, beam splitters, and a microprocessor. The detection system can exist as a separate unit, but is preferably integrated with a controller system into a single instrument. The controller system generally includes a motor for moving the light source and the light detector with relation to the device. Integration of these functions into a single unit facilitates the connection of these instruments to a computer by minimizing the number of communication port(s) required to transmit information between the controller, the detector and the computer. Integration of the detection system with a computer system typically requires software for converting detector signal information into information relating to the location of an optical feature of the device.

Figure 2:
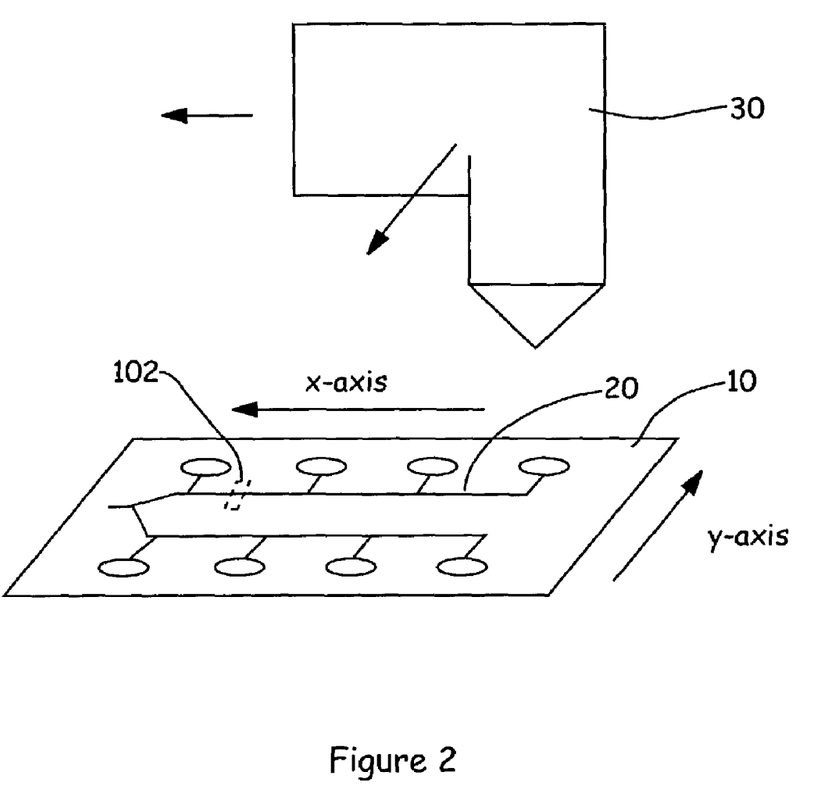
FIG. 2 illustrates the use of an optical detection system with a microfluidic device.

In operation, the devices and systems of the invention perform one or more analytical operations followed by detection of the results of the one or more operations within the detection channel region. FIG. 2 illustrates the use of a microfluidic device with a detector proximal to the detection window. The microfluidic device 10 comprises microscale channels 20 designed to handle small volumes of fluid. Materials to be analyzed are transported along the microscale channel, past a detection window/region 102 where a detectable signal indicative of the presence or absence of some material or condition is measured by detection system 30. The signals within these channels result from the presence of light emitting substances therein. The light emitting substances may be fluorescent or chemiluminescent materials used as indicators of the presence or absence of some material or condition. Detection system 30 is used to measure the amount of light emitted from the fluorescent or chemiluminescent material within the channels 20 of the device 10.

Figure 3:
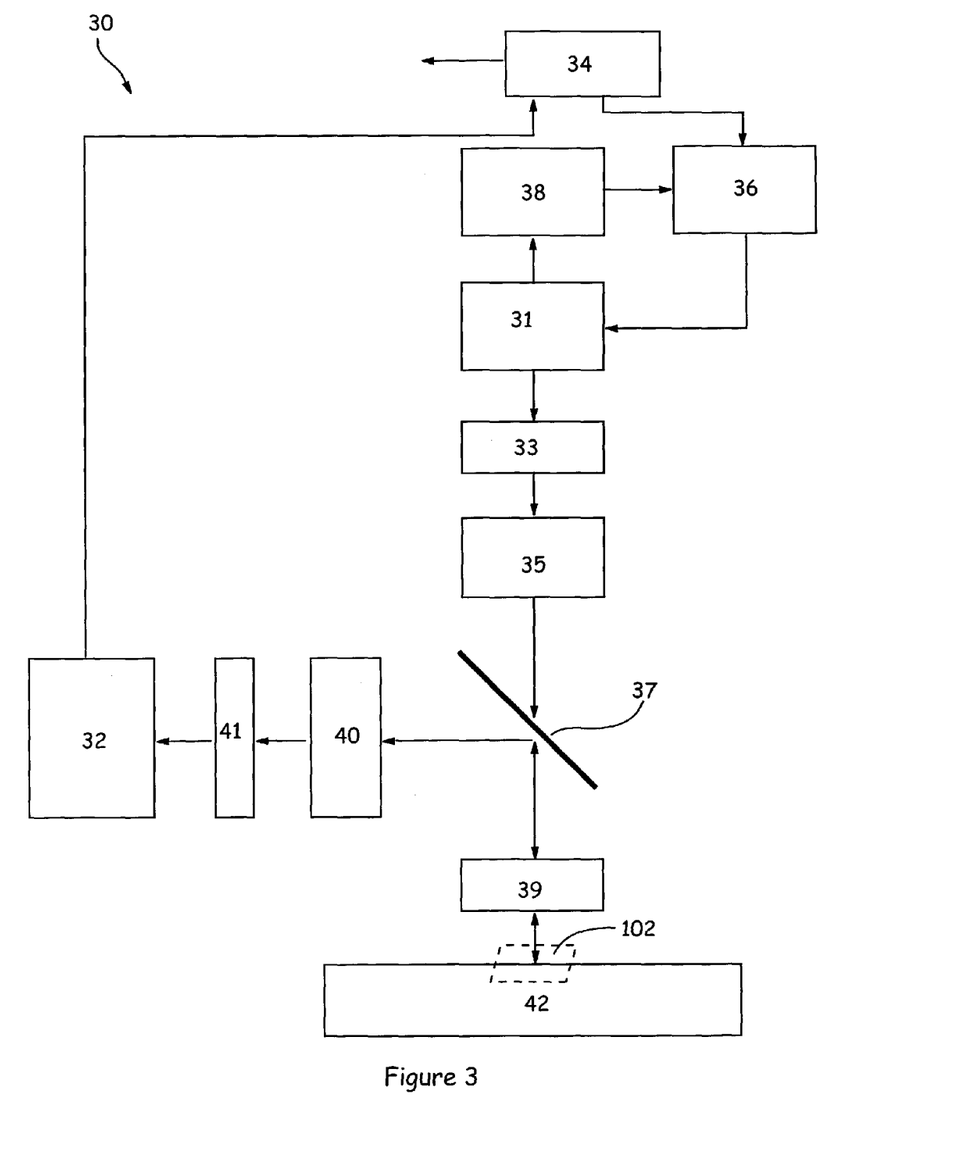
FIG. 3 is a block diagram of a detector used in the method of the present invention.

FIG. 3 shows a block diagram of an embodiment of a detection system used with the methods of the present invention. Detection system 30 may be used, for example, to detect fluorescence induced by exposure to laser radiation. As shown, detection system 30 includes a light source (such as a laser or laser diode) 31 that directs light towards a sample located within a microfluidic device 42, a light detector (such as a PMT) 32 operable to detect light emitted from the sample and to convert the light into electric signals, and a microprocessor 34 that controls the light source, decodes the electric impulses provided by the detector, and transmits the decoded impulses to a host computer (not shown) as data. The light source 31 of the detection system is positioned so that the detection window 102 is disposed in the path of the light emitted by the light source 31, and so that the system is in sensory communication with the desired portion of the microchannel network via the optical detection window 102 disposed over the desired portion of the microchannel network. The light emitted by the light source 31 is directed toward an appropriate location in the microchannel network on the microfluidic device 42 so that it can activate the fluorescent indicator within the desired portion of the microchannel network. As the sample passes the detection region 102, signals produced by the sample materials are detected by detector 32 and sent to microprocessor 34. The light source 31 preferably produces light at an appropriate wavelength for activating fluorescently labeled samples. For example, a red laser diode may be used as the light source in order to facilitate detection of fluorescent species that excite in the red range. Light source 31 may be any number of light sources that provide the appropriate wavelength, including lasers, laser diodes, light emitting diodes (LEDs), and the like. Also, light source 31 may be configured to produce a wavelength suitable for detecting materials other than those that are fluorescently labeled. When the light source 31 is cycled on by the microprocessor 34, the light emitted from the light source 31 passes through a lens 33 that focuses the light, and then through an emission filter 35. The emission filter 35 removes light with undesired wavelengths from the light emitted by the light source 31, primarily passing the wavelengths necessary to excite the selected fluorophores. For example, the emission filter may only allow light having a wavelength between 625 nm and 705 nm to pass therethrough.

After the light passes through emission filter 35, a portion of the light passes through a beamsplitter 37 mounted at a 45-degree angle of incidence to the incoming laser beam. Beamsplitter 37 passes the wavelengths necessary to excite the selected fluorophores while reflecting the undesired wavelengths. In an exemplary embodiment, beamsplitter 37 further filters the light emitted from the light source 31 by permitting only light with wavelength less than 670 nm to pass therethrough. The light that passes through the beamsplitter 37 impinges on the sample within the microfluidic device 42. A lens 39 is provided to focus the beam from the beamsplitter onto the sample. The fluorescence emitted from the sample travels back along the same optical path from the sample to the beamsplitter 37 and is reflected by the beamsplitter towards light detector 32. The beamsplitter 37 filters the light by reflecting the fluorescence light while allowing the excitation light to pass therethrough. A dichroic coating is preferably placed on a surface of the beamsplitter 37 to filter the reflected excitation light from the fluorescence light. Beamsplitter 37 first directs the fluorescent light to a detection filter 40 that further filters the signal emitted from the sample. In an exemplary embodiment, detection filter 40 is configured to allow only light having a wavelength between 645 nm and 665 nm to pass through. Filters suitable for use as the emission filter 35 and detection filter 40 are available from Omega Optical, Inc. of Brattleboro, Vt. A focusing lens 41 is disposed adjacent detection filter 40 to direct the light reflected from beamsplitter 37 into light detector 32.

Light detector 32 converts the incoming light into electric impulses. These electrical impulses are decoded by the microprocessor 34 and sent to the host computer as data. Detection system 30 can be coupled to the host computer via an interface such as a serial data connection, for transmitting detected light data to the computer for analysis, storage, and data manipulation. The light detector 32 may be a photodiode, avalanche photodiode, photomultiplier tube, diode array, or charged coupled device (CCD). Light detector 32 may include, for example, an integrator and an analog-to-digital converter having analog input coupled to an output of the integrator, as described in U.S. Pat. No. 5,959,291.

Although the above description is made with reference to a microfluidic device, one of skill in the art will appreciate that the device could be any other suitable device such as a test tube, capillary tube, a microchannel, or well in a multiwell plate.

III. Methods of Alignment of Detection Optics

As stated above, the methods of the present invention provide a method for aligning the optical components of a microfluidic system. Specifically, the methods provide for positioning a detection system in reference to a microfluidic device so that a signal emitted from a reaction within the device may be detected. In a broad sense, the method for aligning the detection system includes positioning a light beam on a surface of a device, collecting reflected light by a light detector, converting the light signal into data which is further translated into the location of a first optical feature of a device. The methods further provide repeating the steps outlined above to determine the location of a second optical feature of the device, determining the distance between the first and the second optical features of the device, followed by comparing this distance to a preprogrammed layout of the device to compute the precise location of the light detector in reference to the device. Finally, the methods provide transporting the detection system to the targeted region of the device.

Typically, the targeted region may be a detection window disposed over a portion of the microchannel network of a microfluidic device. The light source generates a light beam that travels through a lens, which focuses the light into an optical beam incident on a surface of the device. A controller moves the detection system in a plane parallel to the surface of the device. As the optical beam travels traverses the surface of the device, light reflected off the surface is directed back to the light detector within the detection system to create a background signal. A detectable signal is generated as the light beam coincides with an optical feature of the device. As used herein, an "optical feature" comprises a cavity, channel, reservoir or any other feature that produces a detectable change in the background signal. Suitable detectable signal changes for the methods of the present invention include essentially any change in the signaling characteristics received from the surface comprising the optical features. For example, the detectable signal can include a light emission, a change in light emission, an absorbance, a change in absorbance, a fluorescence, a change in fluorescence, a phosphorescence, a change in phosphorescence, a luminescence, a change in luminescence, a refractive index, refraction, diffraction or the like. In preferred aspects, a light detector such as a photodiode or photo multiplier tube converts the light signals into electrical signals. The electrical signals are decoded by a microprocessor within the detection system and transmitted to a host computer as data.

In embodiments of the methods of the present invention, the detection system collects signals from at least two optical features of the device. The detection signals received from each of the at least two optical features are transmitted to a microprocessor for converting into electrical signals. The electrical signals are then directed to a host computer for computing the distance between the optical features. Generally, the distance between any two optical features of the device may be computed or measured by a number of different methods. In some embodiments, the distance is computed by inputting the speed of travel of the optical beam, the time for the optical beam to travel between the two features and the diameter of the illumination spot that is created when the optical beam coincides with the surface of the device. It will be understood by one of skill that any other suitable method for measuring the distances between the optical features may be used within the present invention. For example, in alternative embodiments the distance could be directly measured by the positioning system. The distance between the at least two optical features is compared to a preprogrammed configuration in order to determine the exact location of the light source in relation to the device. The detection module is then motioned along in a direction perpendicular to the direction in which the distance between the two optical features was measured. After the perpendicular movement, the distance between the between the two optical features is measured again in the original direction. The cycle of perpendicular movement and measurement is repeated until the distance between the two optical features is equal to a preset distance. When the detection module arrives at a distance equal to the preset distance, it is properly aligned with the targeted region of the device. In operation, measurement of the distance between the two points is carried out by system software having one or more logic instructions that direct the system to: (a) receive inputted parameters that delineate the movement of an optical beam across the surface of the device at a given speed (b) measure the amount of time for the beam to move from the first optical feature to the next optical feature (c) receive measured parameters for an illumination spot created when the optical beam is incident on the surface and (d) calculate the distance between the two points from the amount of time, the speed, and the width of the illumination spot. The methods of measurement of distances between the various optical features are described in detail in co-owned U.S. application Ser. No. 10/124,738, filed Apr. 17, 2002.

Generally, the microfluidic devices of the present invention are part of a microfluidic system that is part of a self-contained laboratory instrument. The configuration of the microfluidic system in the instrument may be such that in certain embodiments the detection module is positioned above the microfluidic device while in some other embodiments the detection module is positioned below the microfluidic device. For example, in the Agilent 2100 Bioanalyzer instrument, commercially available from Agilent Technologies (Palo Alto, Calif.), the detection module is generally disposed below the microfluidic device.

Figure 5:
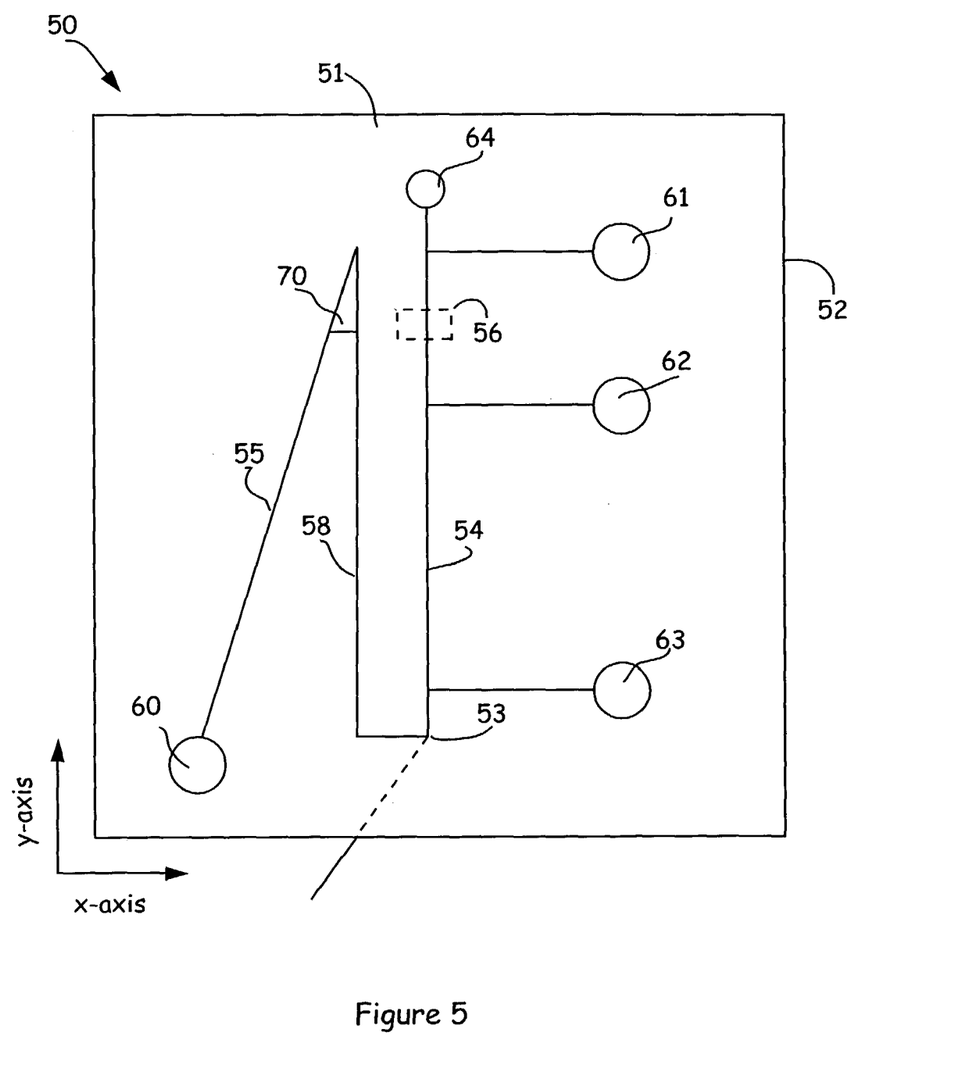
FIG. 5 is a microfluidic device suitable for use with the methods of the present invention.

FIG. 5 provides additional details regarding an example microfluidic device 50 that is in accordance with the methods of the present invention. The view in FIG. 5 looks down on a planar surface 51 of the microfluidic device 50 through a transparent cover plate (not shown) onto the body structure 52 of the device. The body structure 52 of the microfluidic device 50 has a reaction channel 54 and an alignment channel 55 therein. Reaction channel 54 comprises a detection region 56 downstream from the sample introduction intersection 53. Reservoirs 60, 61, 62, 63 and 64 are in fluid communication with the reaction channel 54 and the alignment channel 55. Alignment channel 55 continues into channel region 58, which is coextensive along the y-axis with the reaction channel 54. Microchannel region 58 runs parallel to reaction channel 54. Reaction components such as cells, reagents or dyes and/or other materials are flowed through the channels by applying a vacuum at reservoir 64 (or any other reservoir in the system) and/or by applying appropriate voltage gradients between at least two of the reservoirs 60, 61, 62, 63 or 64.

In the embodiment shown in FIG. 5, a solution comprising a fluorescent dye is added into reservoir 60 and is flowed through the alignment channel 55 and through region 58 toward the reaction channel 54. An optical detection system (not shown) is scanned along the surface 51 of the microfluidic device 50 so that an optical beam generated by the light source within the detection system travels in the direction of the x-axis. When the optical beam is incident on the surface 51 of the body structure, it is reflected back and detected by a light detector such as a photodiode. The signal obtained from the light reflected off the surface 51 forms a threshold or background signal. As the traveling light beam reaches an optical feature, such as the alignment channel 55, the change in the intensity of the reflected light generates a detectable signal. This is recorded as a first signal. When the light beam reaches the microchannel region 58, a second signal is recorded. The computer computes the distance traveled along the x-axis between the first and the second signals. The measured distance is then compared using an algorithm to a stored library of various optical layouts, which could include a known distance 70 between the first and second signals. The known distance 70 occurs at the same location along the y-axis as the detection region 56. If the distance along the x-axis between the first and second signals is not equal to the known distance 70, a controller moves the detection system along the y-axis. After the new location along the y-axis is reached, the distance between the alignment channel 55 and the microchannel 58 is calculated again, and the measured distance is again compared to the known distance 70 between the channels 55, 58. These steps are iteratively repeated one or more times until the detection system reaches a point where the measured distance is equal to distance 70. At this location, the detection system is motioned along the x-axis until it reaches a third optical feature, which will be the detection region 56.

The arrangement of channels depicted in FIG. 5 is merely one possible arrangement of the spatial positioning of the various microchannels and reservoirs. Of course, any arrangement in which a measured dimension may be correlated to a position on the microfluidic device may be used in the present invention. Additional alternatives can be devised, such as by combining the microfluidic elements described herein with other microfluidic device components described in the patents and applications referenced herein.

IV. Method of Identifying a Microfluidic Device

The present invention also provides methods and systems for identifying a microfluidic device. In one embodiment, the invention provides a method of obtaining an optical profile of a microfluidic device whereby a light detector traveling in a plane parallel to a surface of a device detects various optical features on the microfluidic device. These features may be on the surface of the device, or may be visible through a cover layer that is transparent to the wavelength of light being detected. The detection signal received from each of the optical features is transmitted to a microprocessor for conversion into an electrical signal. The electric signal is then directed to a host computer for creating and storing an optical profile of the device. In some embodiments, the light detector detects light reflected from optical features. In other embodiments, the light detector detects fluorescence from a material contained within optical features. In still other embodiments, the light detected in the presence of an optical feature may differ from background levels of light because of a difference in the transmissivity or absorbance of the optical feature, or of a material contained within the optical feature.

In another aspect of the invention, the systems of the present invention comprise a host computer and software for storing and comparing the design configuration of the various optical features of a given device. In yet another aspect, the methods of the present invention provide for identifying a device by comparing an optical profile of the device with a library of preprogrammed profiles of various devices. A detection module scans a surface of the device to provide the optical profile of the device. The optical profile comprises detection signals that are, as previously described, generated when the light beam coincides with the various optical features of the device. The detection signals received when scanning a device are transmitted to a microprocessor that transforms the signals into an optical profile and communicates the profile to a host computer. The host computer stores a library of known optical profiles for multiple devices. The optical profile for a given device is compared with the library of stored profiles. A device is identified by matching the detected profile with a profile stored in the library.

In other embodiments of the invention, a light source that illuminates at least a portion of the microfluidic device is used instead of a light beam, and the light detector comprises a device capable of imaging the illuminated portion of the device. Devices capable of such imaging include digital cameras such as CCD digital cameras. To identify a microfluidic device, the light detector would generate a digital image of the portion of the microfluidic device illuminated by the light source, and the resulting digital image would then be compared to library of stored images.

Embodiments of the method may be employed in instruments such as the Agilent 2100 Bioanalyzer. Generally in these embodiments, a microfluidic device is placed in a fixed location within the instrument. Optionally, based on the detection system employed, an optically detectable material is flowed through the microscale network of the device. The instrument is programmed with software including logic instructions to (a) direct the system controller to move the optical detection system from the left to the right side of the device along a path parallel to the x-axis, (b) detect and store signals from light reflected back from the surface of the device, (c) compare the profile of the device with a library of stored profiles, and (d) identify the matching profile within the stored library.

Although, the above method has been described in regards to a microfluidic device, it will be appreciated that other devices may be identified by comparing their optical profiles to known optical profiles.

V. Systems for Alignment of Detection Optics

A. Computer

Systems in accordance with the invention comprise integrated software and hardware systems for performing the various methods of the invention. In particular, the systems include a computer and system software having one or more logic instructions. In embodiments of the invention, the logic instructions direct the system to (a) receive and store input pertaining to optical profiles of devices (b) control the detection system to travel in relation to a device so as to pass an optical beam along the surface of the device (c) receive and store detection signals created as the optical beam coincides with multiple optical features of the device (d) calculate the distance traveled between two detection signals (e) compare the calculated distance with a stored optical profile and (f) relocate the detection system to travel to a detection region of a device. Alternatively, the system software has additional logic instructions to identify a selected device by performing steps (a) through (d) above, and further to identify a given device by comparing the optical profile to a library of stored optical profiles.

Figure 4:
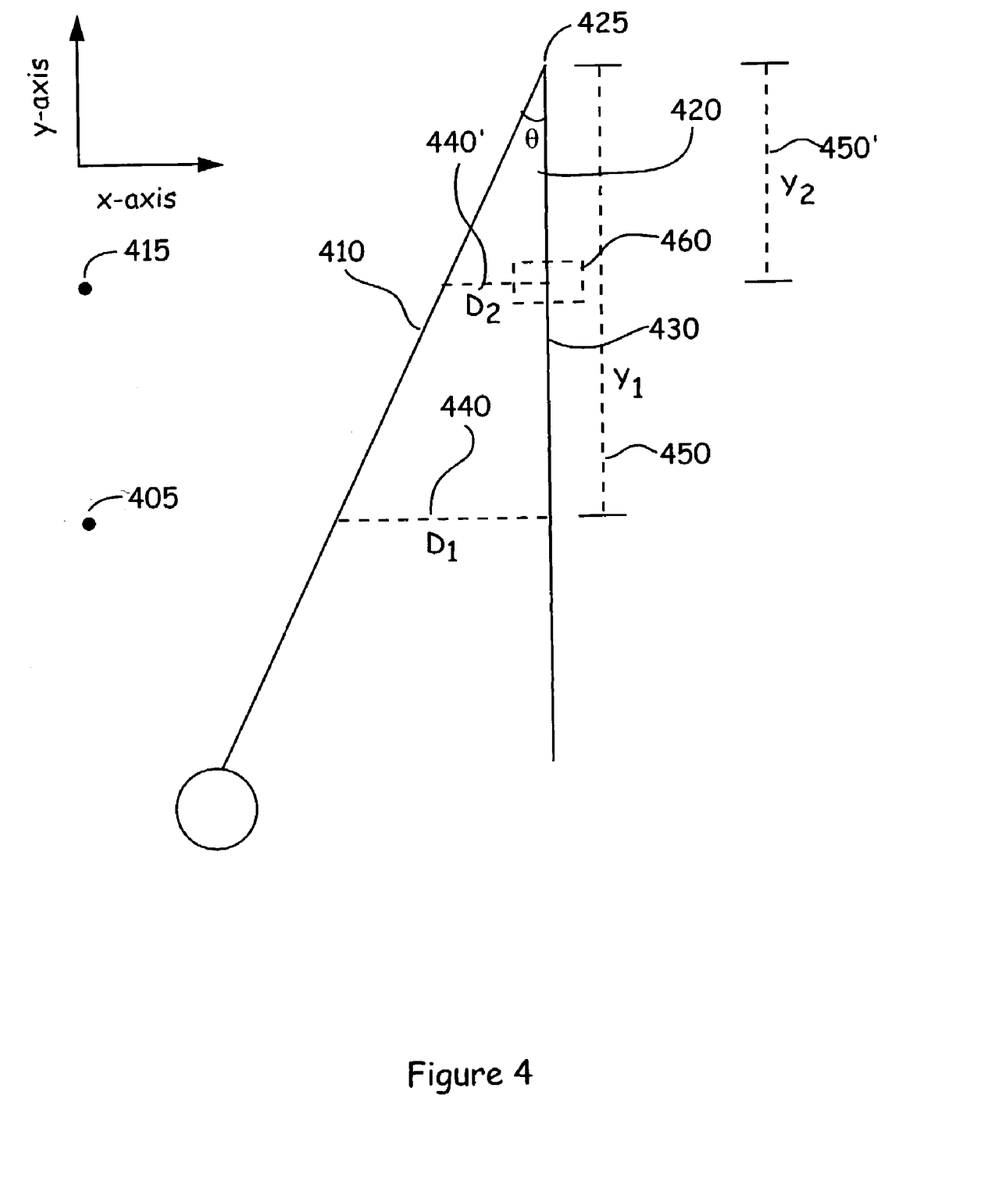
FIG. 4 is a portion of a microfluidic device suitable for use with the methods of the present invention.

The following example illustrates an embodiment of the calculation performed in step (e) above to determine the location of a detection region of a device. FIG. 4 illustrates the layout of optical features of a microfluidic device. The alignment channel 410 forms an angle θ 420 with the detection channel 430. The goal of the logic instructions is to locate the detection system (not shown) directly over the detection region 460 of the detection channel 430. For purposes of illustration, suppose that the detection system is initially located above point 405. The software would direct the detection system to sweep across the surface of the microfluidic device in the direction of the x-axis. During this sweep, the detection system would encounter two optical features as it crosses channels 410 and 430. The software would determine that the distance between channels 410 and 430 in the direction of the x-axis is $D_1$ 440. The stored optical profile for the device in FIG. 4 would indicate that the channels 410 and 430 extend from vertex 425 forming an angle θ 420. The trigonometric relationship between channels 410 and 430 eliminates the need to iteratively search for the location along the y-axis that corresponds to the detection region 460. This is because the distance $y_1$ 450 of the detection system from the vertex 425 can be calculated from the relation $$y_1 = D_1/\tan\theta. \quad (1)$$

The location along the y-axis of the detection region 460, which is designated $y_2$ 450' in FIG. 4, would also be in the stored optical profile of the device. Accordingly, the detection system would be moved a distance $(y_1-y_2)$ along the y-axis toward the vertex 425 to arrive at the same y-axis location as the detection region 460.

To exactly arrive at the detection region 460, the detection system could be moved to a point 415, which is at the detection system's original x-axis location and at the same y-axis location as the detection region 460. The detection system would scan along the x-axis until it encounters a second optical feature, which would be detection channel 430. Alternatively, the detection system could move along the x-axis for a distance $D_2$ 440' after encountering a first optical feature, which would be channel 410. The distance $D_2$ could be calculated from the relation $$D_2 = y_2 \cdot \tan\theta, \quad (2)$$

or the distance $D_2$ could be part of the stored optical profile of the device. In yet another alternative embodiment, the distance $D_2$ could be measured in order to verify that the detection system is located a distance $y_2$ from the vertex 425.

Figure 7:
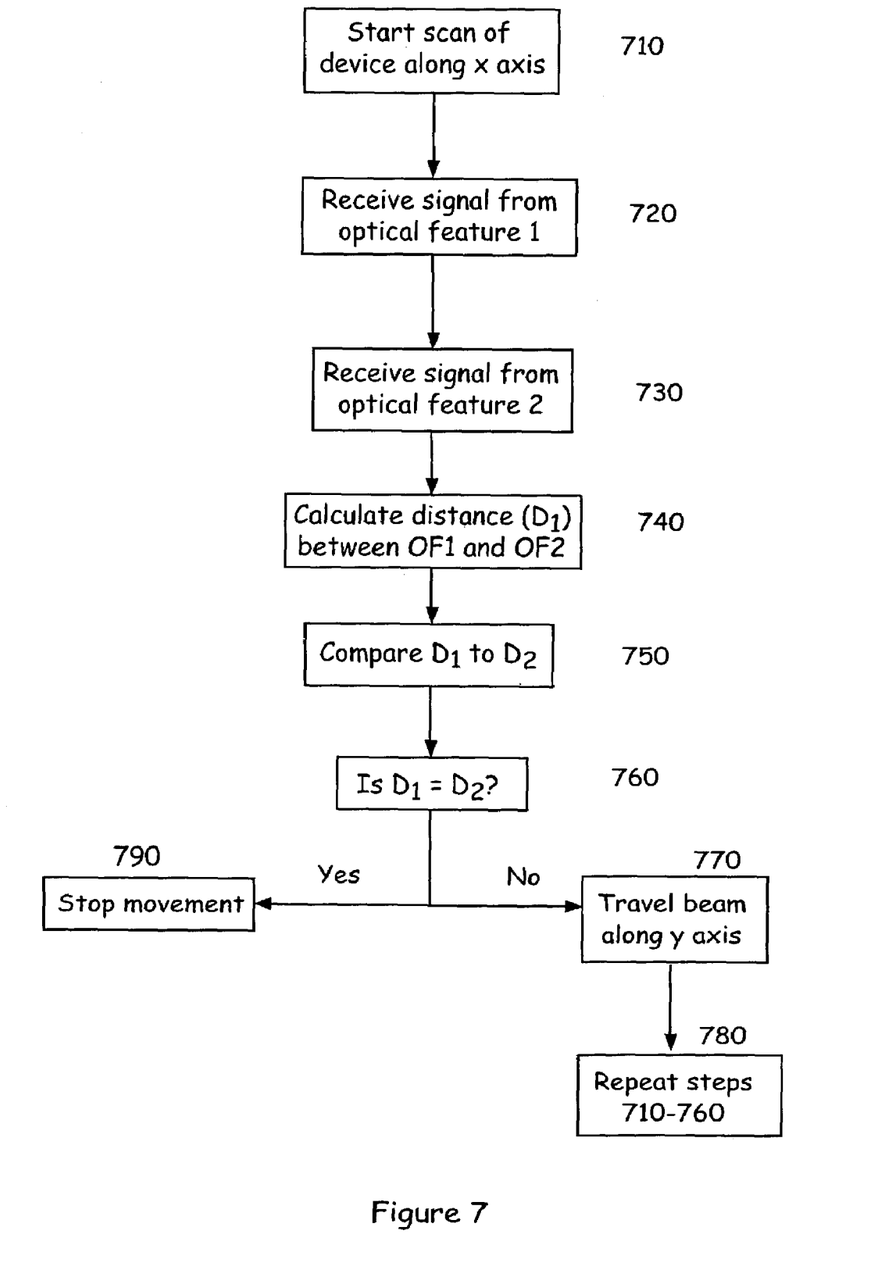
FIG. 7 is a flow chart of an embodiment of one of the methods of the present invention.

FIG. 7 is a flow chart that further schematically illustrates the steps carried out by the computer in an embodiment of the claimed methods. The programmed process begins at step 710, where the computer starts to scan the detection system over the microfluidic device along the x-axis, as was shown in FIGS. 4 and 5. In step 720, the computer receives and stores the detection signal for the first optical feature. In step 730, the computer directs the controller to continue to move the detection system along the x-axis until a second optical feature is detected. Also in step 730 the computer receives and stores the detection signal for the second optical feature. In step 740, the distance between the two optical features is determined. At step 750, the measured distance $D_1$ is compared with a preprogrammed distance $D_2$. At this point, in step 760, if the distance $D_1$ is equal to the preprogrammed distance $D_2$ the computer in step 790 instructs the controller to not move the detection system along the y-axis. On the other hand, if the measured distance $D_1$ is not equal to the preprogrammed distance $D_2$ then in step 770 the computer instructs the system to transport the detection system along the y-axis, and then steps 710 through 760 are repeated until the measured distance between optical feature 2 and optical feature 1 is equal to the preprogrammed distance $D_2$. In other embodiments, the repetition of steps 710 through 760 can be eliminated if the proper location along the y-axis can be calculated from the measured distance $D_1$.

As noted above, the systems of the present invention typically comprise components other than a microfluidic device. For example, overall microfluidic systems in accordance with the invention may also employ a fluid direction and control system that induces and directs the flow of fluids within the microfluidic channel networks. Such flow control systems can induce fluid flow using pressure applied by means of a pressure or vacuum source coupled to one or more ports in the channel network. The microchannel network configuration in the microfluidic device can be optimized to yield a particular flow distribution by applying appropriate pressure differentials between various ports on the device. For example, in some embodiments, a single vacuum source is applied to one port in a microfluidic channel network, and the relative flow resistances of the various channels in the network then determine the relative flow rates in those channels. In alternate embodiments, the flow within the channels of the microfluidic device is controlled by applying multiple pressure and/or vacuum sources to a plurality of different ports of the device to dynamically regulate pressure differentials across different channels of the device. Examples of such multiport pressure controllers are described in U.S. patent application Ser. No. 09/792,435, filed Feb. 23, 2001, published Dec. 20, 2001 as U.S. Published Application Ser. No. 2001/0052460.

In alternative embodiments, the devices of the invention employ electrokinetic material direction systems. Electrokinetic systems typically operate by applying electric fields through channels in order to cause the movement of materials through those channels. Electrokinetic movement can result from one or both of electrophoresis and electroosmosis.

Electrokinetic material direction systems in microfluidic channel networks typically include electrodes placed at the termini of the various channels of the channel network. Often reservoirs or ports are disposed at those termini. Each electrode is coupled to one or more power supplies that deliver controlled electrical currents through the channels of the device to drive the movement of material by means of electrophoresis or electroosmosis, or a combination of the two. Electrokinetic material direction systems are used in the Agilent 2100 Bioanalyzer and associated Caliper Lab-Chip® microfluidic devices. Electrokinetic control of material movement in microfluidic channel networks has been described in detail in, for example, U.S. Pat. Nos. 5,588,195 and 5,976,336. Generally, such systems employ pin electrodes that contact fluid filled reservoirs at the termini of the channels, to deliver electrical current through the various channels of the network. By controlling the magnitude, duration and location of the currents being applied, one can precisely control the direction and velocity of material movement through those channels. In alternate embodiments, electrical circuits can be included on the microfluidic device and are interfaced with controllers via one or more slide connectors. These alternate embodiments can be readily configured to operate in accordance with the present invention.

EXAMPLES

I. Example

Optical Profile for Various Caliper LabChip® Microfluidic Devices Used with the Agilent 2100 Bioanalyzer.

Figure 6A:
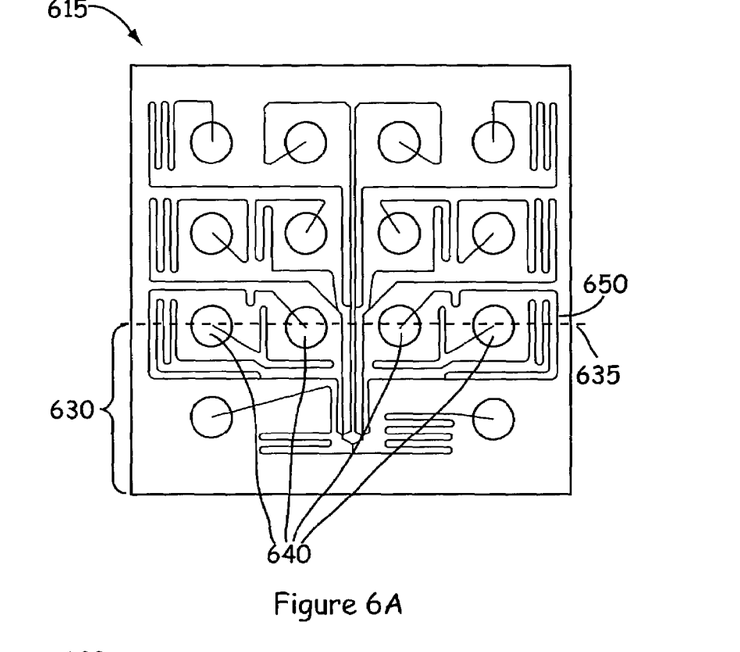
FIGS. 6A and 6B are two different microfluidic devices suitable for use with the methods of the present invention.
Figure 6B:
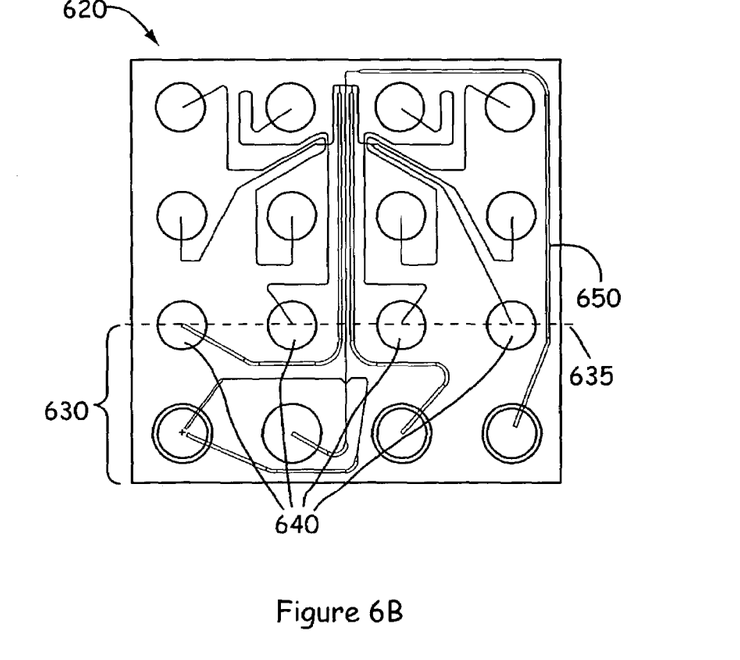
Figure 6C:
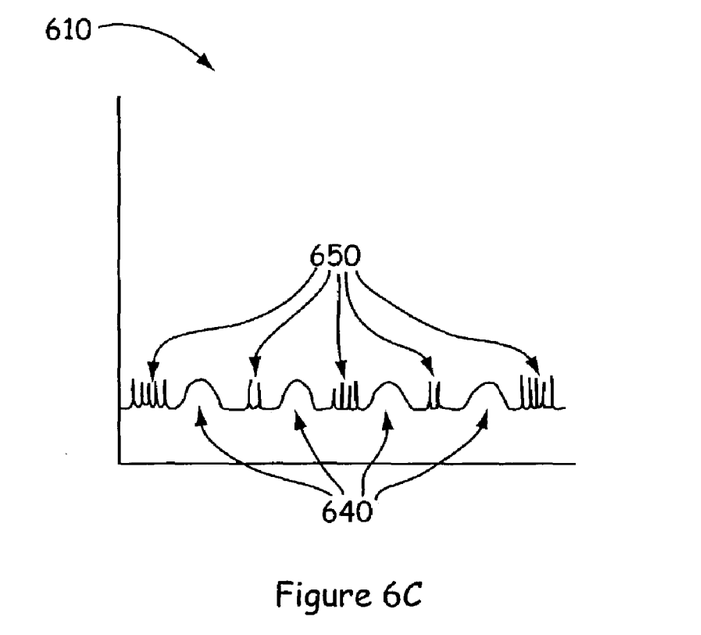
FIGS. 6C and 6D are the optical profiles corresponding to the microfluidic devices in FIGS. 6A and 6B.
Figure 6D:
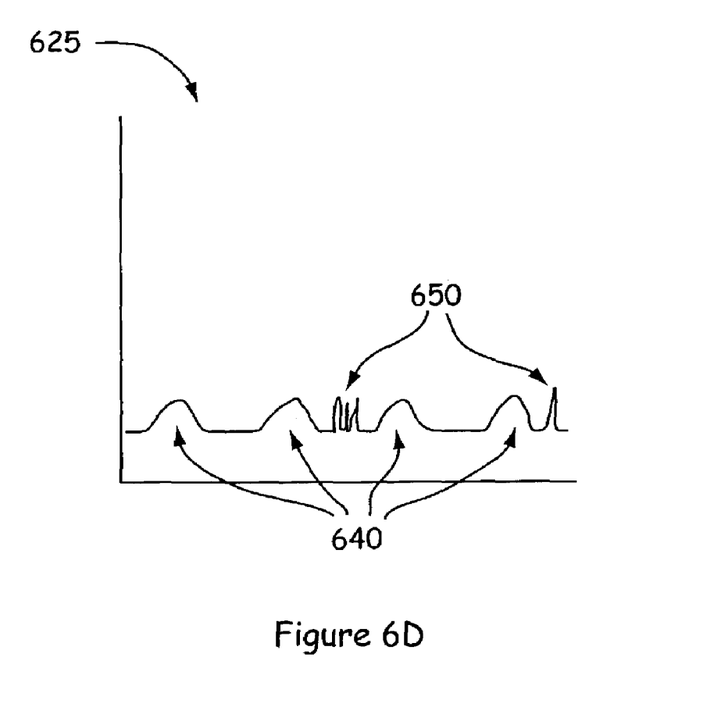

FIGS. 6C and 6D illustrate optical profiles 610 and 625 obtained for the microfluidic devices 615 and 620 in FIGS. 6A and 6B, which can be used with the Agilent 2100 Bioanalyzer. When used in the Agilent 2100 Bioanalyzer, the microfluidic devices 615 and 620 are mounted on a caddy (not shown). The Bioanalzyer is designed to place the caddy in a fixed position. The caddy comprises holes that allow the user to position the caddy on a couple of locator pins on a platform within the Bioanalyzer. During the operation of the Bioanalyzer, the caddy keeps the microfluidic device in a fixed position. The detection system in the Bioanalyzer is located underneath the microfluidic device. By virtue of the fixed position of the microfluidic device, the location of the detector system relative to the microfluidic device is known. Accordingly, as shown in FIGS. 6A and 6B, the detector system can be programmed to scan in the x-axis direction at a predetermined distance 630 along the y-axis. The path followed by the detection system during its scan is illustrated by the dotted lines 635 crossing the microfluidic devices 615 and 620 in FIGS. 6A and 6B respectively. As shown in FIGS. 6C and 6D, the optical profile 610 or 625 for each device is distinguishable from the other device's optical profile. In embodiments of the invention, a computer may be programmed to store a library of optical profiles for a plurality of devices. The devices are identified by comparing the observed optical profile with the profiles stored in the library of optical profiles.

In the present example, a buffer solution containing an intercalating dye such as Cy5™ is flowed through all the microfluidic elements of the devices 615 and 620. A fluorescent detection system is employed to detect the dye. The detection system is scanned across the devices at a fixed distance 630 from the bottom edge of the devices 615 and 620. The dotted lines 635 illustrate the path of the detection system over the devices 615 and 620. The back reflected light was detected and converted into electrical signal to obtain the signature optical profiles for each microfluidic device. As shown in FIGS. 6A, 6B, 6C, and 6D, reservoirs 640 appear as very broad peaks while the microchannels 650 appear as sharp peaks.

While the foregoing invention has been described in some detail for purposes of clarity and understanding, it will be clear to one skilled in the art from a reading of this disclosure that any number of changes in form and detail can be made without departing from the true scope of the invention. For example, all the methods and apparatuses described above may be used in various combinations. All publications, patents, patent applications or other documents cited in this application are incorporated by reference in their entirety for all purposes to the same extent as if each individual publication, patent, patent application, or other document were individually indicated to be incorporated by reference for all purposes.

What is claimed is:

1. A method of positioning an optical detection system with respect to a detection region of a microfluidic device, comprising:
    a) positioning a light beam at a first position along a first axis and along a second axis of said device;
    b) moving the light beam along the first axis from said first position to detect a first optical feature of the device;
    c) moving the light beam along the first axis to detect a second optical feature of the device;
    d) determining a first distance along the first axis between the first and second optical features of the device;
    e) comparing the first distance to a preset distance between the first and second optical features of the device; and
    f) moving the light beam to a second position along the second axis of said device if the measured distance is not equal to the preset distance between the first and second optical features.

2. The method of claim 1, wherein the first and second optical features comprise first and second microfluidic channels.

3. The method of claim 1, wherein said first axis comprises an x-axis of the device.

4. The method of claim 1 wherein said first axis comprises a y-axis of the device.

5. The method of claim 1, further comprising repeating steps (a) through (f) until the first distance is equal to the preset distance between the first and second optical features of the device.

6. The method of claim 1 wherein said detection region is located at the same position along the second axis at which the first distance between said first and second optical features is equal to the preset distance.

7. The method of claim 2, wherein the first and second microfluidic channels comprise a reaction channel and an alignment channel.

8. The method of claim 1, wherein the step of comparing the first distance to a preset distance further comprises calculating the position along the second axis at which the first distance is equal to the preset distance.

9. The method of claim 3, wherein the step of moving the light beam to a second position comprises moving the light beam along a y-axis of the device which is perpendicular to said first axis.

10. The method of claim 1, wherein detecting a first optical feature comprises detecting light reflected from a first optical feature, and detecting a second optical feature comprises detecting light reflected from a second optical feature.

11. The method of claim 1, wherein detecting a first optical feature comprises detecting light emitted from a first optical feature, and detecting a second optical feature comprises detecting light emitted from a second optical feature.

12. The method of claim 11, wherein the emission of light from the first and second optical features results from the fluorescence of a material contained within the first and second optical features.

13. The method of claim 1, wherein detecting a first optical feature comprises detecting a change in transmissivity or absorbance, and detecting a second optical feature comprises detecting a change in transmissivity or absorbance.

14. The method of claim 1 wherein said determining is performed by a computer.

15. The method of claim 14 wherein said computer stores the preset distance between the first and second optical features.

16. The method of claim 1 further comprising moving the light beam to a third optical feature that includes the detection region.

17. The method of claim 16 wherein the third optical feature comprises a microfluidic channel of the device.

* * * * *